United States Patent [19]

Kassebaum et al.

[11] Patent Number: 5,317,003
[45] Date of Patent: May 31, 1994

[54] HERBICIDAL COMPOSITIONS COMPRISING GLYPHOSATE SALTS AND ALKOXYLATED QUATERNARY AMINE SURFACTANTS

[75] Inventors: James W. Kassebaum, Ballwin; Howard C. Berk, St. Louis, both of Mo.

[73] Assignee: Monsanto Company, St. Louis, Mo.

[21] Appl. No.: 914,089

[22] Filed: Jul. 16, 1992

[51] Int. Cl.$^5$ .................... A01N 25/30; A01N 57/04
[52] U.S. Cl. .................................. 504/116; 504/206
[58] Field of Search ............. 71/86, DIG. 1; 504/116, 504/206; A01N 25/30

[56] References Cited

U.S. PATENT DOCUMENTS

| | | | |
|---|---|---|---|
| 3,123,641 | 3/1964 | Longley | 564/294 |
| 3,141,905 | 7/1964 | Longley | 564/294 |
| 4,075,002 | 2/1978 | Drewe et al. | 71/92 |
| 4,159,901 | 7/1979 | Beestman et al. | 71/86 |
| 4,525,200 | 6/1985 | Kimpara et al. | 71/76 |

FOREIGN PATENT DOCUMENTS 0274369 4/1992 European Pat. Off. .

OTHER PUBLICATIONS

J. B. Wyrill and O. C. Burnside "Glyphosate Toxicity to Common Milkweed and Hemp Dogbane as Influenced by Surfactants", *Weed Science*, 25:3 (May 1977) pp. 275–287.

*Primary Examiner*—Allen J. Robinson
*Assistant Examiner*—S. Mark Clark
*Attorney, Agent, or Firm*—Frank D. Shearin

[57] ABSTRACT

A herbicidal composition is provided which is substantially non-irritant to the eyes and which comprises a stable aqueous concentrate solution of one or more agriculturally acceptable salts of N-phosphonomethylglycine and a surfactant represented by the formula

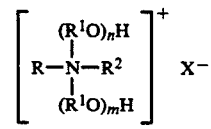

wherein R is an alkyl group having from about 6 to about 14 carbon atoms, $R^1$ is ethyl, propyl, or a mixture of ethyl and propyl, the sum of n and m is between about 5 and about 50, $R^2$ is an alkyl group with 1-4 carbon atoms, X is an agriculturally acceptable anion, and the weight ratio of surfactant to N-phosphonomethylglycine (expressed as the acid equivalent) is between about 1:5 and about 5:1.

14 Claims, No Drawings

HERBICIDAL COMPOSITIONS COMPRISING GLYPHOSATE SALTS AND ALKOXYLATED QUATERNARY AMINE SURFACTANTS

BACKGROUND OF THE INVENTION

This invention relates to herbicidal compositions, and more particularly relates to herbicidal compositions containing one or more N-phosphonomethylglycine salts and a surfactant.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-phosphonomethylglycine and its salts are conveniently applied in an aqueous solution as a post-emergent phytotoxicant for the control of numerous plant species. N-Phosphonomethylglycine and its salts are characterized by a broad spectrum activity, i.e., they control growth of a wide variety of plants.

Commercial formulations of N-phosphonomethylglycine are usually aqueous solutions wherein the N-phosphonomethylglycine is present as a herbicidally acceptable salt, such as an alkali metal salt, the ammonium, alkylsulfonium, or alkylphosphonium salt or the salt of an amine having a molecular weight of less than about 300. The monoisopropylamine salt of N-phosphonomethylglycine is the most widely used salt in such aqueous compositions. In addition, such compositions usually contain a surfactant to enhance the effectiveness of the N-phosphonomethylglycine when it is applied to the foliage of various plants. The most widely used surfactant in commercial compositions is an ethoxylated fatty amine.

It is known to those skilled in the art that a particular surfactant used in an aqueous composition 5 with a herbicide can enhance the effectiveness of the herbicide, whereas other surfactants have very little, if any beneficial effect, and in fact, some may be antagonistic. Wyrill and Burnside, *Weed Science*, Vol. 25 (1977), p 275-287, examined dilute N-phosphonomethylglycine salt solutions containing different classes of surfactants, including polyoxyethylene octadecyl methyl ammonium chlorides containing on average 2 and 15 oxyethylene units (ETHOQUAD 18/12 and ETHOQUAD 18/25, respectively). They did not examine or suggest the use of shorter-chain alkyl methyl ammonium chlorides. Some classes of surfactant were more effective than others in enhancing the herbicidal effect of N-phosphonomethylglycine (used as a solution of the isopropylamine salt), and Wyrill and Burnside concluded that an effective surfactant is a critical component of any aqueous composition containing N-phosphonomethylglycine. For example, ETHOQUAD 18/12 was relatively ineffective in enhancing phytotoxicity of N-phosphonomethylglycine to hemp dogbane, whereas in a separate experiment ETHOQUAD 18/25 was one of the most effective surfactants tested. In the latter experiment, the surfactant was used at a concentration of 1% of the spray solution, a very high concentration by comparison with that delivered by commercial agricultural formulations of N-phosphonomethylglycine at typical application rates in typical spray volumes. The ratio of ETHOQUAD 18/25 to N-phosphonomethylglycine (expressed as acid equivalent) was 6.7:1 at the higher N-phosphonomethylglycine rate applied, and 26.7:1 at the lower rate applied. This compares with surfactant/ N-phosphonomethylglycine ratios typically in the range from 1:4 to 4:1, most commonly around 1:2, delivered by commercial agricultural formulations.

Although certain surfactants may enhance the biological activity of N-phosphonomethylglycine when used at relatively high concentrations in dilute N-phosphonomethylglycine salt solutions (e.g., a tank mix), many of such surfactants are ineffective at low surfactant/N-phosphonomethylglycine ratios. However, it is impossible to incorporate surfactants into highly concentrated aqueous compositions of N-phosphonomethylglycine except at such low ratios. Even then, many surfactants are difficult to coformulate with concentrated aqueous solutions of N-phosphonomethylglycine salts because of adverse effects on viscosity, clarity, high and low temperature stability and other physical characteristics that are desired by the end user. In addition, while N-phosphonomethylglycine and its salts are known to be of very low toxicity and environmentally acceptable, many surfactants are relatively toxic to aquatic life, and/or cause irritation when in contact with the eye.

U.S. Pat. No. 4,075,002 to Drewe et al. and U.S. Pat. No. 4,525,200 to Kimpara et al. each disclose polyoxyethylene alkyl methyl ammonium chlorides in combination with other surfactants in aqueous herbicidal compositions. However, neither of these references disclose the use of polyoxyethylene alkyl methyl ammonium chlorides in a herbicidal composition containing a herbicidally acceptable salt of N-phosphonomethylglycine, nor do they disclose that such herbicidal compositions have reduced eye irritation.

Accordingly, it would be desirable to obtain a stable, concentrated aqueous formulation of N-phosphonomethylglycine which contains a surfactant that at a low ratio of surfactant to N-phosphonomethylglycine is highly effective in enhancing the biological effect of N-phosphonomethylglycine but has lower eye irritation and aquatic toxicity than other surfactants. It has now been found that certain quaternary ammonium compounds are effective at low ratios of surfactant to N-phosphonomethylglycine in enhancing the herbicidal activity of N-phosphonomethylglycine, and that concentrated aqueous formulations of N-phosphonomethylglycine containing such quaternary ammonium compounds are clear, stable, of very low toxicity to aquatic life and virtually non-irritating to the eye.

SUMMARY OF THE INVENTION

These and other advantages are achieved in a herbicidal composition which comprises an aqueous solution of: (a) one or more herbicidally acceptable salts of N-phosphonomethylglycine at an acid equivalent concentration of between about 5 and 40 weight percent; and (b) a surfactant represented by the formula

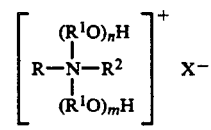

wherein R is an alkyl group having an average of from about 6 to about 20 carbon atoms, $R^1$ is ethyl, propyl, or a mixture of ethyl and propyl, n and m are numbers independently selected from about 2 to about 40 and the sum of n and m is between about 5 and about 50, $R^2$ is an alkyl group with 1 to about 4 carbon atoms, $X^-$ is an agriculturally acceptable anion, and the weight ratio of surfactant to N-phosphonomethylglycine (expressed as acid equivalent) is between about 1:5 and about 5:1.

DETAILED DESCRIPTION OF THE INVENTION

As noted above, N-phosphonomethylglycine is a well-known herbicide, and numerous methods are known in the art for preparing this compound. It is also known in the art that N-phosphonomethylglycine is relatively insoluble in water, and that to prepare concentrated aqueous compositions containing N-phosphonomethylglycine, it is desirable to prepare a herbicidally effective salt of N-phosphonomethylglycine. Such herbicidally effective salts include those of the alkali metals, ammonium, alkylsulfonium, alkylphosphonium or organic amines having a molecular weight below about 300. The isopropylamine salt is preferred.

The surfactants used in the present invention are quaternary ammonium compounds and are known to those skilled in the art. Some of these surfactants are commercially available, such as ETHOQUAD C/25, a polyoxyethylene alkyl methyl ammonium chloride with an average alkyl chain length of about 12 carbon atoms and an average of 15 oxyethylene units, available from Akzo Chemical Company. Such surfactants can be prepared by procedures known to those skilled in the art. In general, these surfactants are prepared by reacting ethylene oxide and/or propylene oxide with a suitable alkylamine having from about 6 to about 20 carbon atoms. These alkyl amines are generally derived from naturally occurring products such as tallow, coconut, soybean or cottonseed oils, and as such are mixtures of different chain lengths. The preferred alkylamines have average chain lengths of about 10 to 14 carbon atoms, for example those derived from coconut oil and known as cocoamines. The procedure to add an alkyl group with 1 to 4 carbon atoms to the nitrogen to form the quaternary ammonium compound is also known to those skilled in the art.

Thus, referring to formula I above, R is an alkyl group having from about 6 to about 20 carbon atoms, and in preferred examples when a cocoamine is used as a starting material, R averages about 10 to 14 carbon atoms. $R^2$ is an alkyl group having 1 to 4 carbon atoms, and is preferably methyl. When the amine is reacted with ethylene oxide, $R^1$ is ethyl, and when propylene oxide is used to react with the amine, $R^1$ is propyl. When both ethylene oxide and propylene oxide are used, $R^1$ can be a mixture of ethyl and propyl. Preferred surfactants are those wherein $R^1$ is ethyl, and even more preferred are those wherein $R^1$ is ethyl, $R^2$ is methyl and a cocoamine is used, i.e., wherein R averages about 10 to 14 carbon atoms.

The mole equivalents of oxyalkylene to the moles of amine, i.e., the value of n plus m in the above formula, can vary within wide limits. Generally, n and m vary independently. Surfactants used in the compositions of the invention have a mole equivalent ratio of oxyalkylene to amine between about 5 and about 50, but a mole equivalent ratio between about 10 and about 20 is preferred.

As will occur to those skilled in the art, any number of anions can be used in the surfactant used in the present invention, provided that such anions do not cause compatibility problems in the composition or cause eye irritation. Phosphates and halides are preferred, and chloride is especially preferred.

In the compositions of the present invention, the weight ratio of surfactant to N-phosphonomethylglycine (expressed as its acid equivalent) can vary over a wide range, for example, from about 1:5 to about 5:1. The optimum ratio will vary according to the manner in which the herbicidal composition is applied, the weed species to be treated, and the particular surfactants selected, but normally a weight ratio between about 1:4 and about 2:1, for example 1:2, provides satisfactory results over a wide range of weed species with most of the surfactants of the present invention.

The compositions of the present invention are aqueous concentrates containing from about 5 to about 40 weight percent of N-phosphonomethylglycine acid equivalent. The composition is diluted with water to form a spray solution containing from about 0.1 to about 2% N-phosphonomethylglycine for application to the foliage of plants. The compositions of the present invention are preferred when the concentration of N-phosphonomethylglycine is between about 20 and about 35 weight percent.

When the most preferred surfactants are used, a further unexpected advantage is that no additional solubilizing agent such as a glycol is necessary to prevent the surfactant from gelling when added to water. optionally, however, compositions of the invention can contain additional glycols such as polyethylene glycol having a molecular weight of about 400 (PEG-400). Other optional additional ingredients include ammonium salts, for example ammonium sulfate, and active ingredients such as 2,4-dichlorophenoxyacetic acid, dicamba, acifluorfen and the like.

As will occur to those skilled in the art, the present compositions can contain surfactants in addition to the surfactant set forth in the above formula. It is only necessary that the composition containing such additional surfactant is substantially non-irritating to the eye, and does not substantially decrease the biological effectiveness of the composition. Such additional surfactants for use in the present composition include; ethoxylated and/or propoxylated tertiary alkylamines, ethoxylated and/or propoxylated quaternary alkylamines that fall outside the above formula, ethoxylated primary or secondary alcohols, ethoxylated acetylenic diols, fatty acids, ethoxylated fatty acids, alkyl aryl ethoxylates, alkylpolyglycosides, sugar esters, glycerol esters, sorbitan esters, and the like. Mixtures of surfactants that fall within the above formula can also be used, as well as mixtures of additional surfactants with the surfactant of the above formula. However, the weight ratio of total surfactant to N-phosphonomethylglycine (expressed as the acid equivalent) should be maintained between about 1:5 and about 5:1, preferably between about 1:4 and about 2:1.

The relative eye irritation of aqueous concentrate formulations of N-phosphonomethylglycine containing alkylamine surfactants is not readily predictable. Most such surfactants, when present at concentrations of about 10% or more in the formulation, cause the formulation to be moderately to severely irritant to the eyes. In general there is little or no difference between the quaternary amine surfactant and its corresponding tertiary amine analog in this respect. For example, in a comparison of formulations containing 10% by weight respectively of a tertiary cocoamine ethoxylate with an average of 2 moles of ethylene oxide per mole of amine (ETHOMEEN C/12, available from Akzo Chemicals, Inc., Chicago, Ill.) and of a quaternary N-methyl cocoammonium chloride ethoxylate with an average of 2 moles of ethylene oxide per mole of amine (ETHOQUAD C/12, also available from Akzo Chemicals, Inc.), both were found to be equally irritant.

The basis of the present invention is the unexpected discovery that surfactants of the formula shown above wherein R (the alkyl backbone) has an average from about 6 to about 20, preferably from about 10 to about 14, carbon atoms and the degree of ethoxylation (n+m) has an average of about 5 to about 50, preferably from about 10 to about 20, give formulations of much lower eye irritation than the corresponding tertiary analogs (not quaternized with the $R^2$ alkyl group) of these surfactants. It is also unexpected that formulations of N-phosphonomethylglycine containing the most preferred surfactants of the invention are of very low toxicity to fish, similar in herbicidal efficacy to the best commercial N-phosphonomethylglycine formulations and of excellent physical stability at low and high temperatures without the need for additional glycols as solubilizing agents.

The invention is further illustrated by, but not limited to, the following examples.

EXAMPLES 1-3

A series of aqueous compositions are prepared for comparison with a standard outside the scope of the present invention, as summarized in Table 1. These examples of the invention contain as surfactant a polyoxyethylene quaternary alkyl methyl ammonium chloride derived from coconut oil and having an average of 15 moles of ethylene oxide per mole of amine (ETHOQUAD C/25). The standard contains a polyoxyethylene tertiary alkylamine derived from coconut oil and having an average of 15 moles of ethylene oxide per mole of amine (ETHOMEEN C/25), together with a small amount of PEG-400, a polyethylene glycol having an average molecular weight of about 400, which is necessary to prevent the surfactant from gelling when added to water. All examples and the standard contain the monoisopropylamine salt of N-phosphonomethylglycine at a concentration of 31% by weight, expressed as acid equivalent.

TABLE 1

| Example No. | Surfactant Identity | Weight % | PEG-400 Weight % |
|---|---|---|---|
| 1 | ETHOQUAD C/25 | 11.0 | 0 |
| 2 | ETHOQUAD C/25 | 17.5 | 0 |
| 3 | ETHOQUAD C/25 | 19.0 | 0 |
| Standard | ETHOMEEN C/25 | 11.0 | 2.75 |

The compositions of Examples 1-3 all were clear solutions with cloud points higher than 60° C. In extensive greenhouse, growth chamber and field testing, the efficacy of the composition of Example 1 has been shown to be similar to that of ROUNDUP ® herbicide, a commercial formulation containing 31% N-phosphonomethylglycine together with an ethoxylated tallowamine surfactant. As would be expected by those skilled in the art, the compositions of Examples 2 and 3 with higher concentrations of surfactant have been shown to be somewhat more efficacious than the composition of Example 1.

EXAMPLE 4

A standard eye irritation test was carried out using the compositions of Examples 1-3 and the standard shown in Table 1 (Environmental Protection Agency assessment guidelines, subsection F, *Hazard Evaluation: Human and Domestic Animals* (Revised ed. 1984) Section 81-4, *Primary Eye Irritation*). The standard gave results which would place it in the most severely irritant class (Category I) used by the USA Environmental Protection Agency in classifying pesticidal formulations. By comparison, the composition of Example 1, which contains the same concentration of surfactant as the standard, gave results which would place it in the least irritant class (Category IV). Both the compositions of Example 2 (Category III) and Example 3 (Category II) were markedly less irritant to the eyes than the standard, in spite of their much higher surfactant content.

EXAMPLE 5

The composition of Example 1 was examined for toxicity to trout by the procedure of *OECD Guidelines for Testing of Chemicals*, Test no. 203 "Fish Acute Toxicity Test" for April 1984. The result showed that this composition had very low toxicity to trout (LC50 of greater than 100 mg/l). When assessed on the proposed toxicity rating scale for use at Columbia National Fisheries Research Laboratory, USA, the composition of Example 1 is classified as "relatively non-toxic". Although the invention has been described in terms of specific embodiments which are set forth in considerable detail, it is understood that this is by way of illustration only, and that alternative embodiments and operating techniques will become apparent to those skilled in the art in view of the disclosure. Accordingly, modifications can be made without departing from the spirit of the described invention.

What is claimed is:

1. A herbicidal composition which comprises a stable aqueous concentrate solution of: (a) one or more agriculturally acceptable salts of N-phosphonomethylglycine at an acid equivalent concentration of between about 5 and about 40 weight percent; and (b) a surfactant represented by the formula

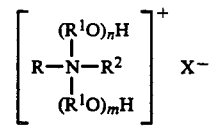

wherein R is an alkyl group having an average of from about 6 to about 14 carbon atoms, $R^1$ is ethyl, propyl or a mixture of ethyl and propyl, n and m are numbers independently selected from about 2 to about 40, and the sum of n and m is about 5 and about 50, $R^2$ is between an alkyl group having 1 to 4 carbon atoms, $X^-$ is an agriculturally acceptable anion, and the weight ratio of surfactant to N-phosphonomethylglycine (expressed as the acid equivalent) is between about 1:5 and about 5:1.

2. A composition of claim 1 wherein $X^-$ is a halide or a phosphate.

3. A composition of claim 2 wherein $X^-$ is chloride.

4. A composition of claim 1 wherein R has an average of from about 10 to about 14 carbon atoms.

5. A composition of claim 1 wherein $R^2$ is methyl.

6. A composition of claim 1 wherein $R^1$ is ethyl.

7. A composition of claim 1 wherein $R^2$ is methyl and the sum of n and m is between about 10 and about 20.

8. A composition of claim 7 wherein the surfactant is a polyoxyethylene alkyl methyl ammonium chloride derived from coconut oil.

9. A composition of claim 1 or claim 8 wherein the weight ratio of surfactant to N-phosphonomethylglycine (expressed as the acid equivalent) is between about 1:4 and 2:1.

10. A composition of claim 1 or claim 8 wherein the salt of N-phosphonomethylglycine is present at an acid equivalent concentration of between about 10 and about 40 weight percent and the weight ratio of surfactant to N-phosphonomethylglycine (expressed as the acid equivalent) is between about 1:4 and about 2:1.

11. A composition of claim 1 or claim 8 which contains an additional surfactant and wherein the weight ratio of total surfactant to N-phosphonomethylglycine (expressed as the acid equivalent) is between about 1:5 and about 5:1.

12. A composition of claim 1 or claim 8 which contains an additional surfactant and wherein the weight ratio of total surfactant to N-phosphonomethylglycine (expressed as the acid equivalent) is between about 1:4 and about 2:1.

13. A composition of claim 1 or claim 8 which contains an additional surfactant selected from the group consisting ethoxylated and propoxylated tertiary alkylamines, ethoxylated and propoxylated quaternary alkylamines, ethoxylated primary alcohols, ethoxylated secondary alcohols, ethoxylated acetylenic diols, fatty acids, ethoxylated fatty acids, alkyl aryl ethoxylates, alkylpolyglycosides, sugar esters, glycerol esters and sorbitan esters, wherein the weight ratio of total surfactant to N-phosphonomethylglycine (expressed as the acid equivalent) is between about 1:5 and about 5:1.

14. A composition of claim 1 or claim 8 wherein the agriculturally acceptable salt of N-phosphonomethylglycine is the monoisopropylamine salt.

* * * * *

UNITED STATES PATENT AND TRADEMARK OFFICE
CERTIFICATE OF CORRECTION

PATENT NO.    :   5,317,003
DATED         :   May 31, 1994
INVENTOR(S)   :   James W. Kassebaum and Howard C. Berk It is certified that error appears in the above-identified patent and that said Letters Patent is hereby corrected as shown below:

In claim 1, column 6, bridging lines 57-58, before "an" and following the second occurrence of "is", please delete "between".

In claim 1, column 6, line 57, before "about" and following the first occurrence of "is", please insert --between--.

On the title page, under the heading labeled "Abstract", please delete "X" and insert therefor --$X^-$--.

In column 1, line 38, before "with" and following "composition", please delete "5".

In column 4, bridging lines 27-28, before "however" and following "water", please delete "optionally" and insert therefor --Optionally--.

In column 6, bridging lines 29-30, before "the" and following "non-toxic", please begin a new paragraph with "Although".

Signed and Sealed this

Twenty-third Day of December, 1997

Attest:

BRUCE LEHMAN

*Attesting Officer*      Commissioner of Patents and Trademarks